US00PP34046P2

(12) United States Plant Patent
Jernigan

(10) Patent No.: US PP34,046 P2
(45) Date of Patent: Mar. 22, 2022

(54) ***LOROPETALUM* PLANT NAMED 'CANRL01'**

(50) Latin Name: *Loropetalum chinense*
Varietal Denomination: CANRL01

(71) Applicant: Brian J. Jernigan, Dearing, GA (US)

(72) Inventor: Brian J. Jernigan, Dearing, GA (US)

(73) Assignee: Center for Applied Nursery Research, Inc., Dearing, GA (US)

( * ) Notice: Subject to any disclaimer, the term of this patent is extended or adjusted under 35 U.S.C. 154(b) by 0 days.

(21) Appl. No.: 17/300,270

(22) Filed: May 5, 2021

(51) Int. Cl.
*A01H 5/12* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/00
See application file for complete search history.

*Primary Examiner* — Anne Marie Grunberg
(74) *Attorney, Agent, or Firm* — James R. Holm

(57) ABSTRACT

A new and distinct *Loropetalum* plant named 'CANRL01' particularly distinguished by a compact, semi-prostrate growth habit, dark burgundy colored foliage that retains its color throughout the year, and medium, dark pink colored flowers, is disclosed.

4 Drawing Sheets

Figure 1:
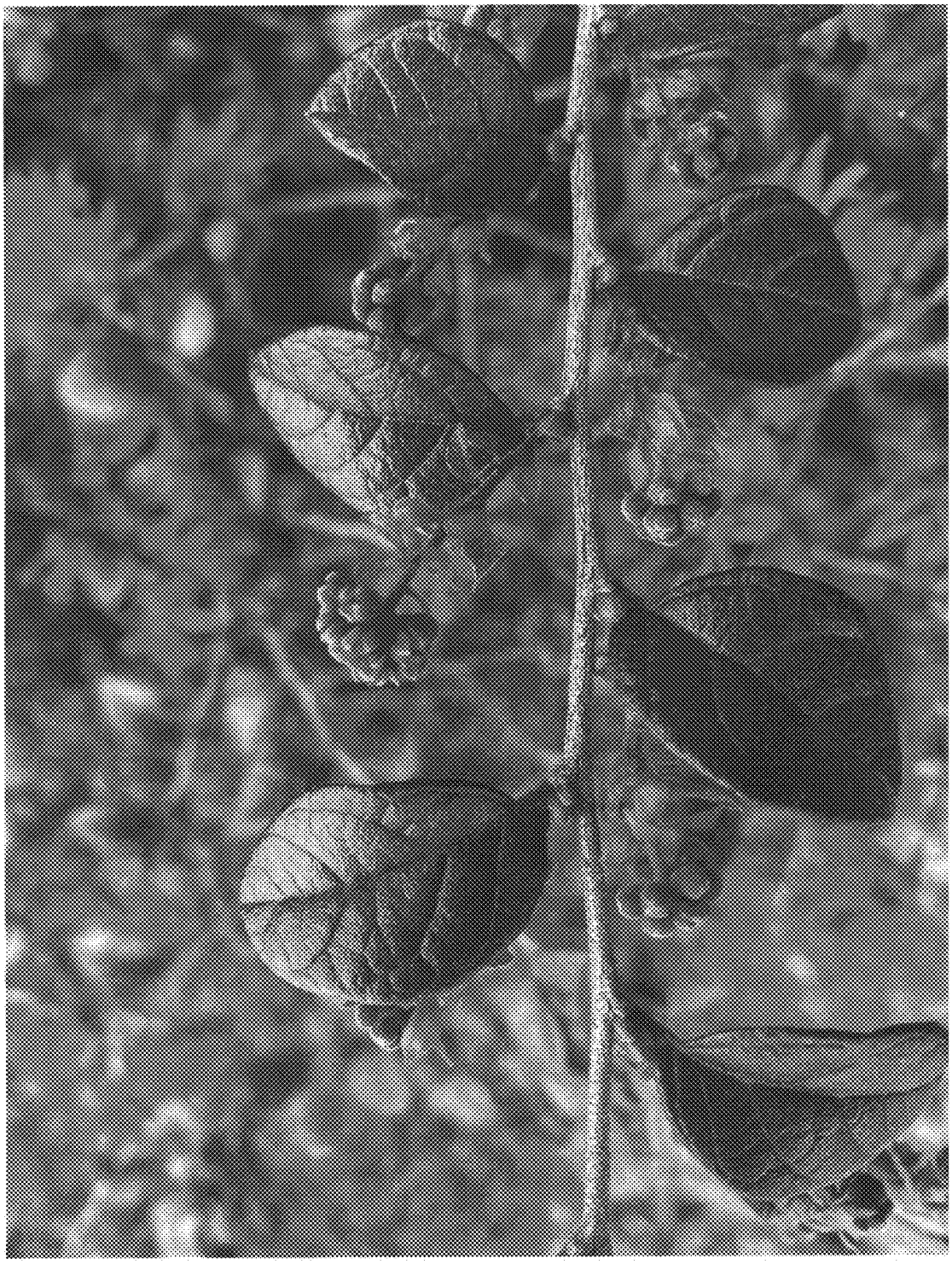

Genus and species: *Loropetalum chinense.*
Variety denomination: 'CANRL01'.

BACKGROUND OF THE NEW PLANT

The present invention comprises a new and distinct variety of *Loropetalum* plant, botanically known as *Loropetalum chinense*, and hereinafter referred to by the variety name 'CANRL01'. This new *Loropetalum* plant originated from an open pollination conducted in the spring of 2011 in Dearing, Ga. between the female *Loropetalum* plant 'Chang Nian Hong' (unpatented) and an unknown male *Loropetalum* plant. The objective of the breeding program was to create new, easier to grow *Loropetalum* plants having unique flower colors and with improved plant growth habits.

Progeny seeds resulting from said open pollination were collected in the fall of 2011. These seeds were sown in June of 2012 and allowed to grow. The new variety was selected by the inventor as a single plant within progeny plants grown in a controlled environment in Dearing, Ga. The new variety was selected based on its medium dark pink colored flowers and overall improved plant growth characteristics as compared to other commercially available *Loropetalum* cultivars. 'CANRL01' was first reproduced asexually by vegetative semi-softwood stem cuttings in July 2014 in Dearing, Ga. 'CANRL01' has been found to retain its distinctive characteristics and has been found to be stable and reproduce true-to-type through three successive generations of asexual reproduction by vegetative semi-softwood stem cuttings.

Plant Breeder's Rights for this variety have not been applied for. 'CANRL01' has not been made publicly available or sold anywhere in the world prior to the effective filing date of this application.

SUMMARY OF THE INVENTION

The new *Loropetalum* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Loropetalum* variety when grown under normal horticultural practices in Dearing, Ga. The combination of these characteristics distinguishes 'CANRL01' as a new and distinct variety of *Loropetalum:*

1. Compact, semi-prostrate growth habit;
2. Burgundy colored foliage that retains its color throughout the year; and
3. Medium, dark pink flower color.

DESCRIPTION OF THE PHOTOGRAPHS

This new *Loropetalum* is illustrated by the accompanying photographs which show the overall plant habit including flowers and foliage of the plant. The colors shown are as true as can be reasonably obtained by conventional photographic procedures. The photographs are of 2, 4 and 6-year-old plants grown in ground and in 2.5 inch and 3-gallon containers in Dearing, Ga. The photographs were taken in Dearing Ga. under natural light and natural shade. Colors in the photographs may differ slightly from the color values cited in the botanical description which accurately describes the colors of the new variety.

FIG. 1. shows the flower buds.

Figure 2:
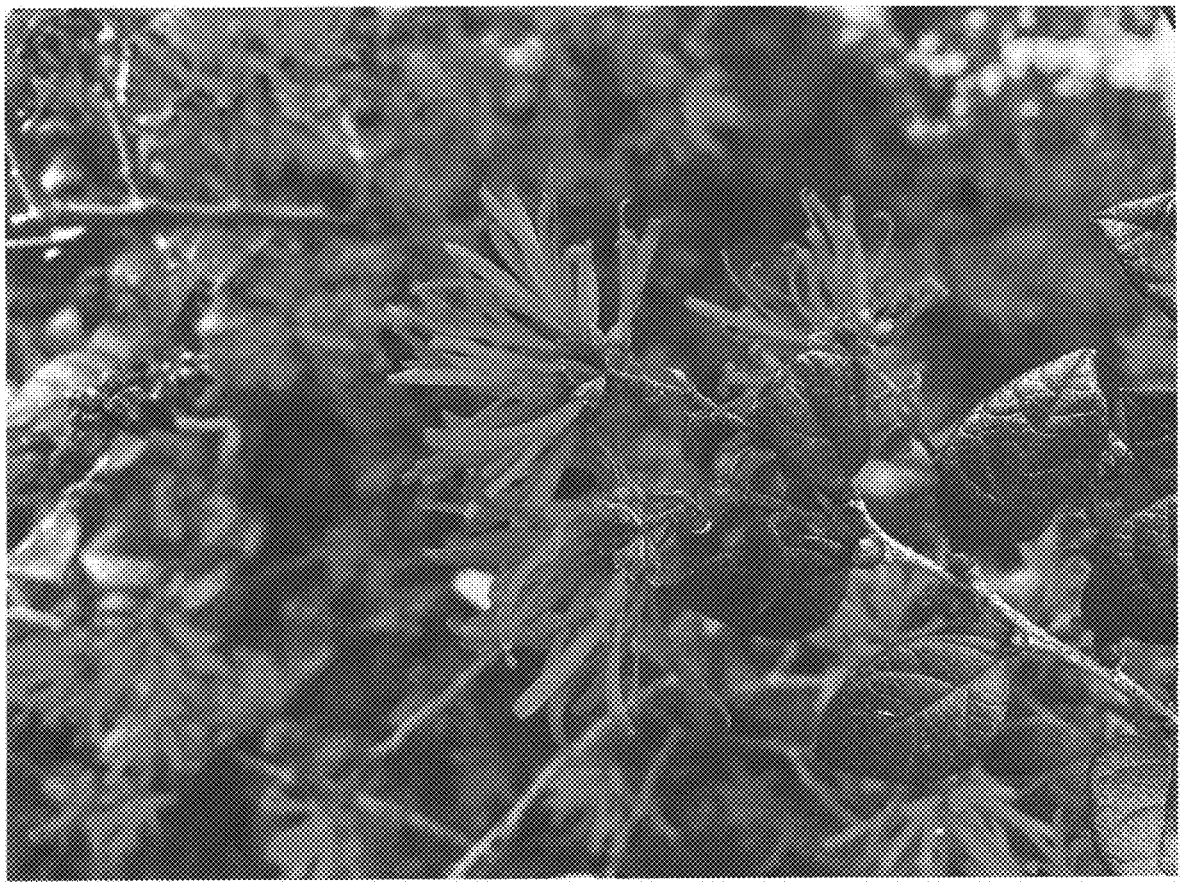

FIG. 2. shows typical, open flowers.

Figure 3:
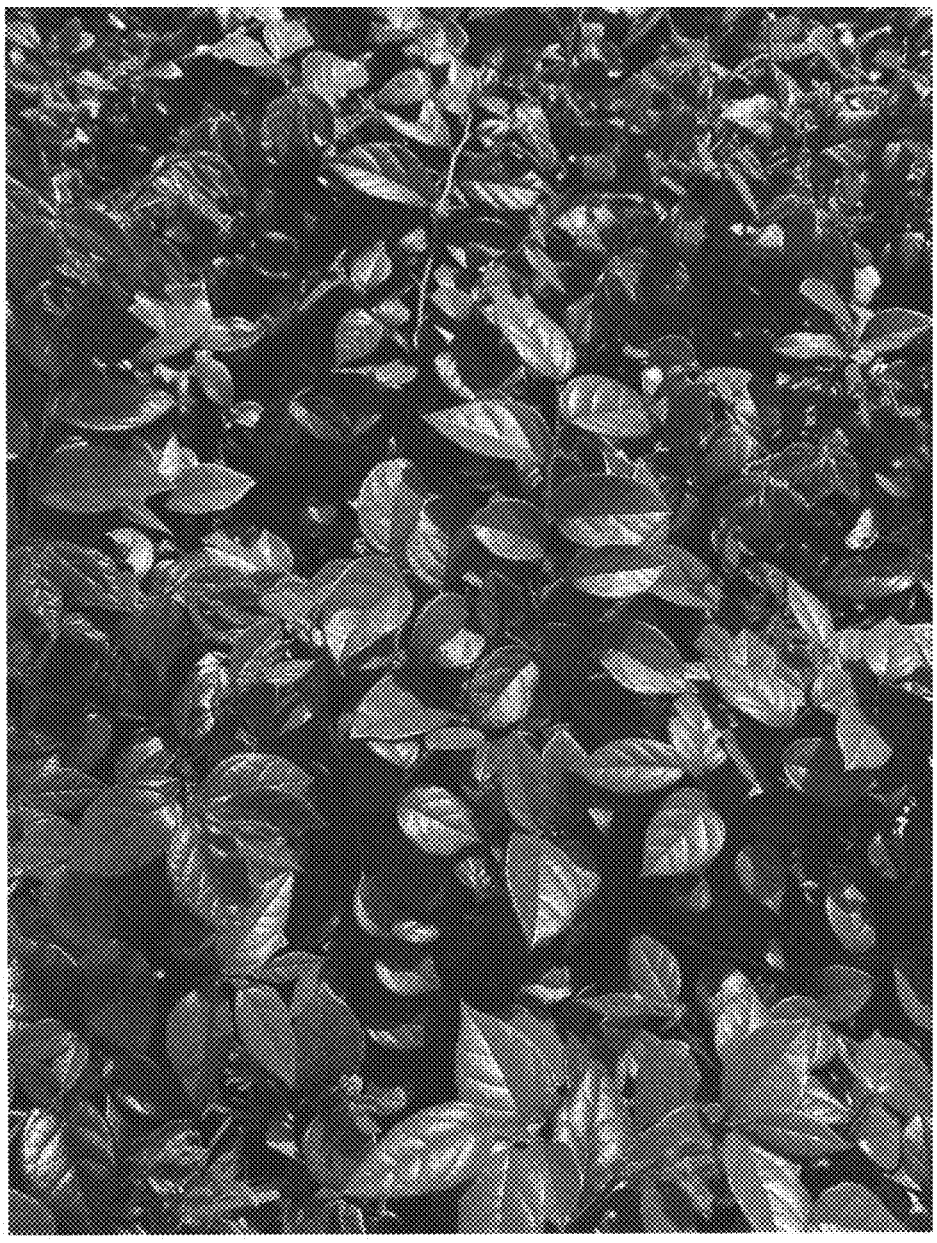

FIG. 3. shows new foliage growth when grown in a shaded environment.

Figure 4:
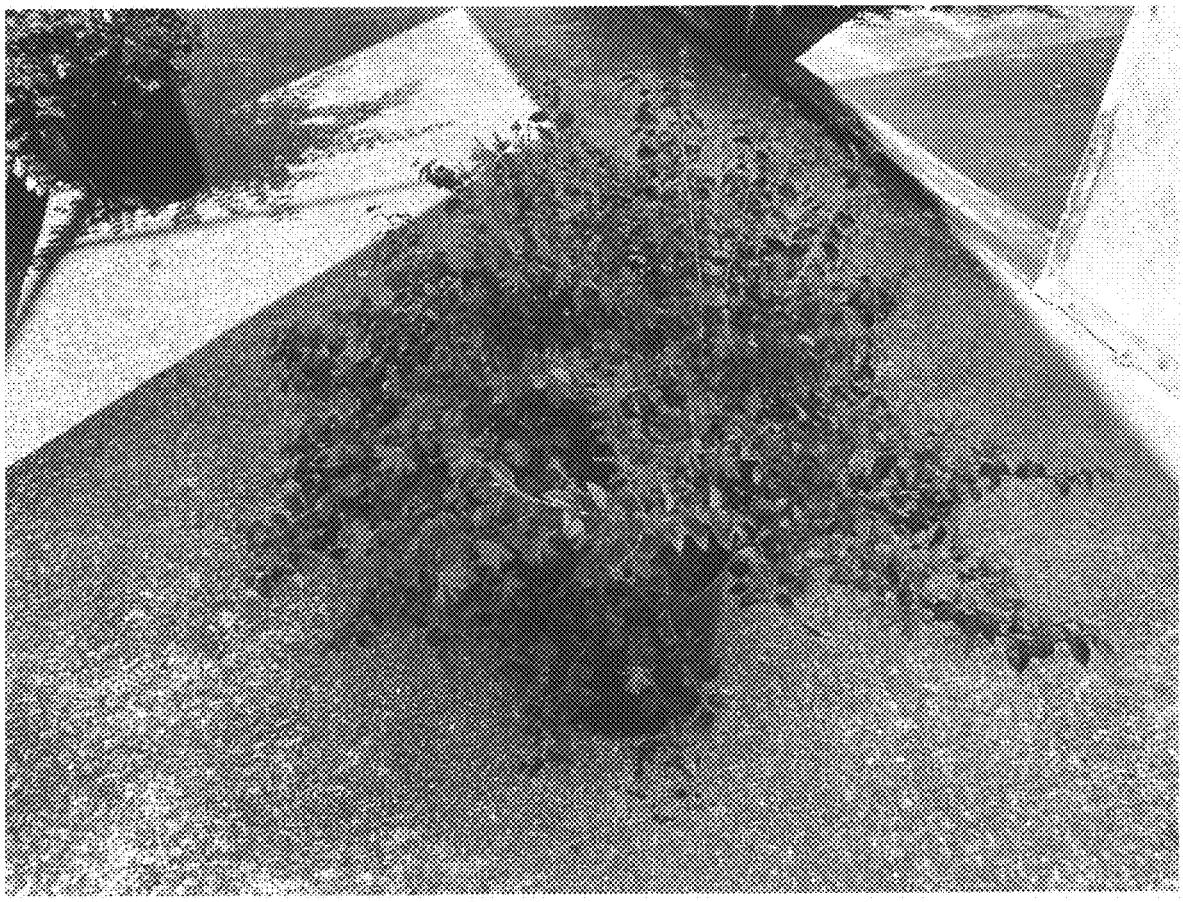

FIG. 4. shows overall plant growth habit when grown in 3-gallon containers.

DESCRIPTION OF THE NEW VARIETY

In the following description, color references are made to The Royal Horticultural Society Colour Chart, Sixth Edition, except where general terms of ordinary dictionary significance are used.

The following observations and measurements describe plants grown outdoors under a natural photoperiod in full sun in Dearing, Ga. Some observations were made indoors under artificial lighting using the aid of a dissecting microscope. Detailed descriptions were taken from February 2018 through March 2021 from 4 and 6-year-old plants grown in ground and from 2-year-old plants grown in 3-gallon containers. Measurements and numerical values represent averages of typical plant types.

DETAILED BOTANICAL DESCRIPTION

Classification:

*Family*.—Hamamelidaceae.

*Botanical.—Loropetalum chinense.*

*Common.—Loropetalum.*

*Denomination*.—'CANRL01'.

Parentage:

*Female or seed parent.—Loropetalum chinense* plant 'Chang Nian Hong' (unpatented).

*Male or pollen parent*.—Unknown.

Propagation:

*Type*.—Vegetative semi-softwood stem cuttings.

*Time to initiate roots.*—2 to 3 weeks under intermittent mist.

*Time to produce a rooted young plant.*—4 months when placed in rooting media in the early summer period of May to June.

Root description: Medium fleshy, fibrous and freely branching; at 3.0 cm from the apex, roots are colored purple, N77A.

Plant description:

*Plant type*.—Perennial shrub.

*Growth habit*.—Overall semi-prostrate with occasional arching branches.

*Height.*—25.0 cm when grown in a 3-gallon container and 72.0 cm on a 6-year-old plant when grown in ground.

*Plant spread.*—75.0 cm when grown in a 3-gallon container and 180.0 cm on a 6-year-old plant when grown in ground.

*Growth rate*.—Moderate.

*Plant vigor*.—Moderate.

*Branching habit*.—Lateral branching.

*Characteristics of primary lateral branches*.—Length: Average of 23.5 cm, ranging from 9.0 cm to 94.0 cm in length. Diameter: Primary branches are 1.0 cm after one year's growth; secondary branches are 0.5 cm after one year's growth. Quantity: Highly branched, 77 percent of nodes are branched. Strength: Young branches are pliable, becoming stiff and breakable as branches transition into semi-hardwood stage of growth. Internode length: 1.07 cm. Color: Young branches: Greyed-purple, 187A. Mature branches: Grey-brown, N199B, becoming greyed-orange, 166A, when branches begin to exfoliate. Prevalence of pubescence: Heavy stellate pubescence on young branches less than one year in age, no pubescence observed on branches aged one year and older. Aspect: Secondary branches range from a 30 to 80 degree angle from primary branches.

Foliage description:

*Leaf arrangement*.—Simple, alternate.

*Average mature leaf size*.—Length: 2.53 cm. Width: 1.74 cm.

*Mature leaf shape of blade*.—Ovate.

*Leaf apex*.—Primarily acute with a mucro.

*Leaf base*.—Oblique.

*Leaf margin*.—Entire.

*Leaf texture (both upper and lower surfaces)*.—Stellate.

*Leaf appearance*.—Upper surface: Glossy. Bottom surface: Matte.

*Leaf color*.—Young leaves: Upper surface: Greyed-Purple, 187A. Lower surface: Purple, B77B. Mature leaves: Upper surface: Greyed-purple, N186A, to yellow-green, 147A, and greyed-purple, 187A. Lower surface: Greyed-purple, N187B, to greyed-purple, N187C, and greyed-green, 188B.

*Leaf venation*.—Type: Pinnate. Color: Upper surface: Greyed-purple, 187A to yellow-green, 148D. Lower surface: Greyed-purple, 185D, to yellow-green, 148D.

*Petiole*.—Length: 0.2 cm. Color: Greyed-purple, N186A to greyed-purple, 184A.

Inflorescence description:

*Bloom period*.—Primary bloom period is typically early spring (February to March) in Dearing, Ga.; blooming occurs sporadically through spring and into fall.

*Flower type*.—Perfect.

*Arrangement and aspect*.—Terminal umbels outward facing at apex of lateral branches.

*Quantity of flowers per lateral branch.*—9 to 12.

*Quantity of flowers per plant*.—Over 2000 on a six-year-old plant.

*Buds*.—Shape: Obovate to obconical. Length: 3.0 mm. Diameter: 2.0 mm. Color: Red-purple, 59A. Prevalence of pubescence: Heavily stellate.

*Petals*.—Quantity per flower: 4. Shape: Linear to slightly curved. Margin: Entire. Texture: Smooth, silky. Appearance: Slightly shiny. Length: 15.0 mm. Width: 1.5 mm. Tip shape: Acute to slightly retuse. Color: Red-purple, 60B.

*Sepals*.—Quantity per flower: 4. Appearance: Matte. Texture: Lightly pubescent, stellate. Arrangement: Whorl. Shape: Ovate and fused at the base, slightly reflexed outward at apex. Length: 2.0 mm. Width: 1.5 mm. Tip aspect: Slightly reflexed, obtuse to acute. Base: Fused. Margin: Entire. Color: Immature (both upper and lower surfaces): Red-purple, 59B. Mature (both upper and lower surfaces): Red-purple, 60A.

*Stamens*.—Quantity: 4 to 5, occasionally up to 7. Color: Red-purple, 59B. Length: 1.0 mm. Width: 0.5 mm. Filaments: Quantity: 4 to 5. Color: Red-purple, 59B. Length: Less than 0.5 mm. Anthers: Shape: Linear. Color: Red-purple, 59B. Length: Most are less than 0.5 mm and occasionally up to 1.0 mm.

*Pollen*.—Amount: Moderate. Color: Greyed white, 156D.

*Pistils*.—Quantity: 2. Color: Red-purple, 59B. Styles: Length: Less than 0.5 mm. Color: Red-purple, 59B. Stigmas: Shape: Irregularly star shaped. Color: Red-purple, 59B.

*Ovaries*.—Size: Approximately 1.5 mm at the time of pollination. Color: Red-purple, 59B.

Cold tolerance: Hardy to USDA zone 7.

Disease and pest tolerance: Tolerance to root diseases has been observed, but has not been tested under controlled conditions. Susceptibility or resistance to pests and disease is expected to be similar to other *Loropetalum* cultivars.

Fruit and seed set: None observed.

Drought tolerance: Drought tolerance has not been tested under controlled conditions. Drought tolerance is expected to be similar to other *Loropetalum* cultivars.

COMPARISON WITH PARENTAL VARIETIES

'CANRL01' differs from the female parent plant 'Chang Nian Hong' (unpatented) in that 'CANRL01' has a semi-prostrate growth habit and medium dark pink colored flowers, whereas 'Chang Nian Hong' has a mounding, more upright growth habit and larger, more dark burgundy colored foliage and darker red colored flowers.

COMPARISON WITH KNOWN CULTIVARS

When 'CANRL01' is compared to the commercial *Loropetalum* cultivar 'Peack' (U.S. Plant Pat. No. 18,441), 'Peack' has a more prostrate growth habit and lighter pink colored flowers and lighter burgundy colored foliage.

I claim:

1. A new and distinct variety of *Loropetalum* plant named 'CANRL01', substantially as illustrated and described herein.

* * * * *